(12) United States Patent
Fernandez

(10) Patent No.: US 9,499,367 B2
(45) Date of Patent: Nov. 22, 2016

(54) DEVICE FOR APPLYING A PRODUCT TO SKIN

(71) Applicant: The Dial Corporation, Scottsdale, AZ (US)

(72) Inventor: James A. Fernandez, Chandler, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 14/596,310

(22) Filed: Jan. 14, 2015

(65) Prior Publication Data

US 2016/0200537 A1   Jul. 14, 2016

(51) Int. Cl.
| | |
|---|---|
| B32B 7/12 | (2006.01) |
| B32B 38/10 | (2006.01) |
| B44C 7/00 | (2006.01) |
| A61M 35/00 | (2006.01) |
| B65H 37/00 | (2006.01) |
| B65H 16/00 | (2006.01) |

(52) U.S. Cl.
CPC .......... *B65H 16/005* (2013.01); *A61M 35/003* (2013.01); *B65H 37/007* (2013.01); *B65H 2801/00* (2013.01)

(58) Field of Classification Search
CPC ... B65C 11/00; B65C 9/0006; B65C 9/1865; B65H 11/0004; B65H 11/004; B65H 37/005; B65H 37/007; Y10T 156/1052; Y10T 156/1064; Y10T 156/1788; Y10T 156/1795; A61M 35/003
See application file for complete search history.

(56) References Cited

U.S. PATENT DOCUMENTS

| | | | | |
|---|---|---|---|---|
| 4,917,929 A | * | 4/1990 | Heinecke | A61F 13/023 428/121 |
| 7,731,954 B2 | * | 6/2010 | Davis | A61F 13/00063 424/94.4 |
| 2004/0182962 A1 | * | 9/2004 | Koreska | B65H 37/007 242/370 |
| 2008/0017323 A1 | * | 1/2008 | Peterson | B65H 37/005 156/540 |
| 2008/0302487 A1 | * | 12/2008 | Goodman | A61B 17/085 156/523 |

FOREIGN PATENT DOCUMENTS

FR      EP 1834914 A1 * 9/2007 .......... A61M 35/003

* cited by examiner

*Primary Examiner* — Alex Efta
(74) *Attorney, Agent, or Firm* — David K. Benson

(57) ABSTRACT

A device is provided for applying a product to the skin. The device includes a tape with a layer of the product disposed on a surface of the tape. The device includes a support. A portion of the tape passes over the support such that the tape is between the support and the product. When the tape moves across the skin, the product transfers from the tape to the skin and the tape advances.

4 Claims, 4 Drawing Sheets

DEVICE FOR APPLYING A PRODUCT TO SKIN

FIELD OF THE INVENTION

The present invention generally relates to a device for applying a product to skin and more particularly relates to a device that moves a tape with the product on one surface along the skin of a user.

BACKGROUND OF THE INVENTION

Skin is exposed to and covered with a variety of materials and microbes, including bacteria. When a product is applied to the skin, the bacteria may transfer to the applicator. Under some conditions, the transferred microbes may multiply, further contaminating the applicator. These microbes may then be applied to the skin during subsequent applications.

Additionally, it may be challenging and time consuming to apply a uniform coating of a product to the skin. When the product is medicinal, such non-uniform application may result in under dosing or over dosing of portions of the skin. As a result, some medications may be dispensed at concentrations below optimal to reduce risk of overdose.

Accordingly, it is desirable to have a device that allows local application of a product to the skin while preventing contamination of the application device. In addition, it is desirable to have a device that provides a simple, consistent, controlled thickness for a topically applied product. Furthermore, other desirable features and characteristics of the present invention will become apparent from the subsequent detailed description of the invention and the appended claims, taken in conjunction with the accompanying drawings and this background.

BRIEF SUMMARY OF THE INVENTION

A system is provided for applying a product to the skin. The system includes a tape with the product on one surface of the tape. The tape passes over a support, such that the tape is between the product and the support. The support presses a product surface of the tape against the skin. As the system advances across the skin, the tape advances, transferring the product to the skin.

A device is provided for applying a product to the skin. The device includes a tape having the product disposed on one surface of the tape. The tape passes over an applicator wheel such that the tape is between the applicator wheel and the product. The applicator wheel supports a portion of the tape against the skin to facilitate transfer of the product from the tape to the skin.

A device for applying a product to skin where the device includes a housing. The housing includes a tape with the product disposed on one surface of the tape. A portion of the tape is in a tape supplier which provides the tape to a support. A portion of the tape passes over the support such that the tape is between the support and the product, allowing the product to transfer to the skin. The used tape is received by a tape collector.

BRIEF DESCRIPTION OF THE DRAWINGS

The present invention will hereinafter be described in conjunction with the following drawing figures, wherein like numerals denote like but not necessarily identical elements.

Figure 1:
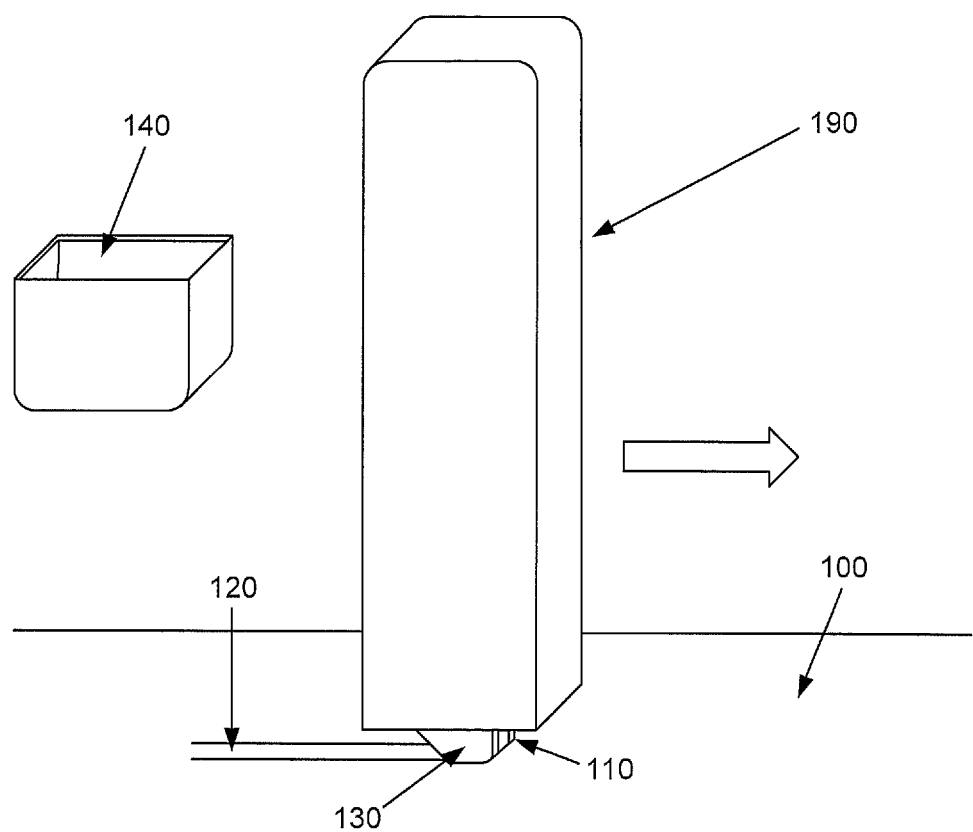
FIG. 1 is an isomorphic diagram of a device for applying a product to skin according to one example of the principles described herein.

The figures illustrate various examples of the present disclosure and do not limit the scope of the claims.

DETAILED DESCRIPTION OF THE INVENTION

The following detailed description is merely exemplary in nature and is not intended to limit the invention or the application and uses of the invention. Furthermore, there is no intention to be bound by any theory presented in the preceding background or the following detailed description.

Skin is covered with a variety of materials and microbes, including bacteria. When a product is applied to the skin, the bacteria may transfer to a device that applies the product. Under some conditions, the transferred microbes may multiply. These bacteria may then be re-applied to the skin during subsequent applications. Moreover, uniform deposition of the product may be difficult, resulting in uneven, and in some cases under dosing or over dosing of the product.

Accordingly, the present disclosure describes devices and systems for applying a product to the skin. The product may include a wide variety of different materials that are placed on the skin, such as medicines, beauty products, cosmetics, and skin treatments, among other topically applied products. The product is placed on a tape. The tape is then loaded into a dispenser. The tape runs across a support outside the dispenser, such that the tape is between the product and the support. The dispenser is placed against the skin and moved along the skin. As the dispenser moves, the product is transferred from the tape to the skin and the tape advances revealing unused tape with more product.

The device of the present specification may have a number of benefits. For example, the device may allow for a consistent thickness of the product to be delivered to the skin. Also, application using the device may be performed using a single hand. Still further, the product may be applied without mess as the product is transferred directly from the tape to the skin. Doing so avoids the mess of creams and pastes that are applied with the fingers. Additionally, application of the product via the device of the present specification avoids contamination of the container that stores the product. For example, the tape is used a single time and does not contact the skin after application. In some examples, the used tape is collected in a separate area of the device to avoid cross contamination with an unused portion of the tape and the deposited product.

The support may be a rotating wheel that supports the tape against the skin. The support may be fixed relative to the device. The support may have a flat upper portion or may have a point or rounded surface to press the tape against the skin.

The device may include a tape supplier that stores the unused tape until it is advanced to the application site on the support. The device may also include a tape collector that sequesters the used tape. The tape supply may be a wheel mounted on an axis in the device housing. The tape collector may also be a wheel mounted on an axis in the device housing. These two wheels may have flanges on either surface to keep the tape on the wheel. In other examples, the walls of the device housing may keep the tape on the wheel. The tape supplier, tape collector, and an applicator wheel may be interconnected such that movement of one component moves one or both of the other components. Such interconnected motion may be accomplished using belts, gears, or other mechanical components. A wide variety of component placements and device geometries are possible. For example, the different components may be different sizes and may be mounted adjacent to each other or separated from one another. In some examples, pins inside the molded housing of the device route the tape between the components and the support. The use of pins may save space or reduce the number of parts used in the device while enabling a wide variety of device geometries.

The device may include a cap that covers a portion of the device. More specifically, the cap may protect the tape and product when not in use. The cap may also help reduce contamination of the device, accidental transfer of the product while not in use, accidental advancement of the tape, and evaporation of the product. The cap may be removable or attached by a hinge to the device. The cap may include a reflective surface, such as a mirror, to facilitate application of the product.

The product on the tape may include multiple layers. For instance, the product may include a therapeutic layer containing an active ingredient and a sealing layer to reduce evaporation of the product or to provide mechanical protection of the product. The upper layer may provide color or decoration, similar to that found on decorated adhesive bandages. The decoration may include color, characters, shapes, team names, logos, symbols, or similar material. Makeup, temporary tattoos, stencils, henna patterns, etc. may be prepared in advance on the tape and then rapidly applied to the skin.

While the product may be applied in a uniform layer using the disclosed device, the product may also be placed on the tape with varying thickness or even gaps to create a variety of the dosing curves and aesthetic effects. For example, shapes designed to conform to the anatomy or sized to cover blemishes are alternatives to a uniform band of applied product.

As demonstrated herein, a device that uses an advancing tape with product disposed thereon allows for the product to be applied to a skin surface without contaminating the device and providing a uniform thickness of the product to the skin. Additionally, the device may provide for clean and simple application of the product.

Additional elements such as an area or mechanism for collecting the used tape within the device, a supply of tape disposed within the device, a cap, multiple layers on the tape, and other elements are described herein which provide additional functionality.

FIG. 1 is an isomorphic diagram of a device (190) for applying a product (120) to skin (100) according to one example of the principles described herein. While FIG. 1 depicts a particular geometry of the device (190), the device (190) may have any number of geometries. As the device (190) is moved across the skin (100) the product (120) is deposited onto the skin (100). A support (130) presses tape (110) against the skin (100). The product (120) to be applied to the skin (100) is disposed on the skin-contacting surface of the tape (110). As the tape (110) comes off the skin (100), the product (120) is transferred to the skin (100) where it remains behind in a uniform thickness layer. Also shown in FIG. 1, is a cap (194) which covers the exposed tape (110) and support (130) when not in use.

Figure 3:
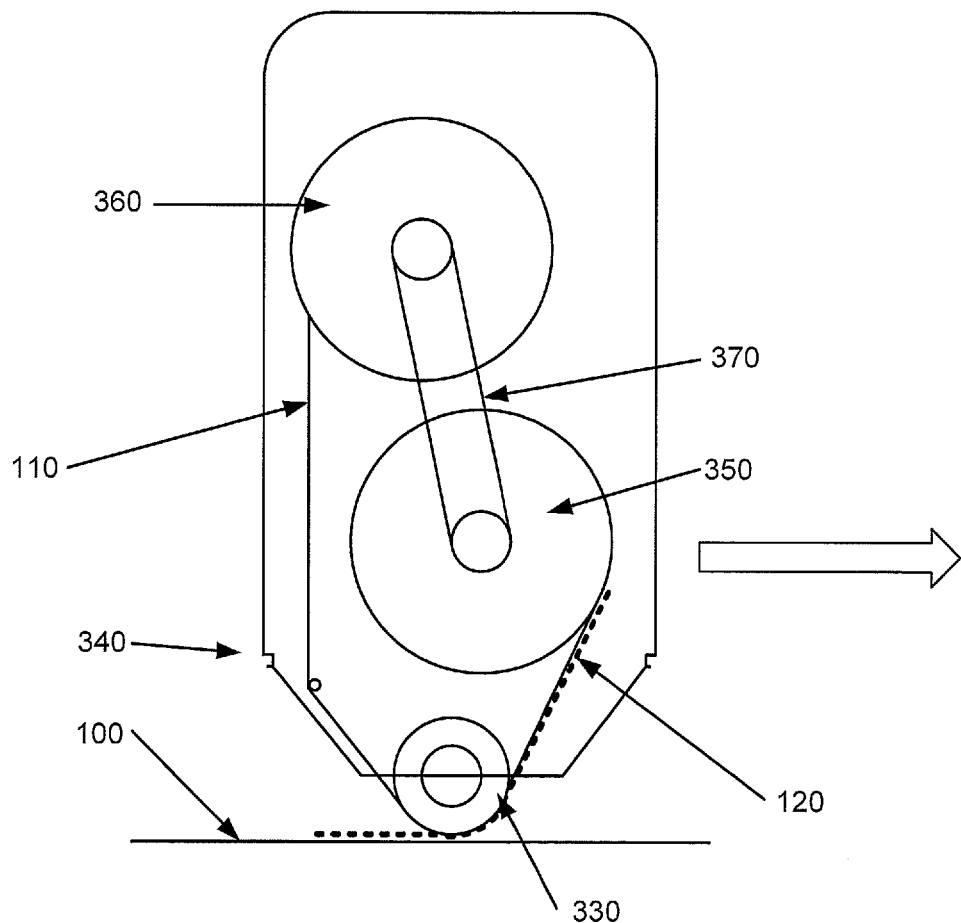
FIG. 3 is a cross sectional diagram of a system for applying product to skin according to one example of the principles described herein.

While the device (190) is shown as an elongated rectangle, a large number of geometries are possible. For example, the device (190) may be pen-like and may be held between the forefinger and the thumb. In another example, the device (190) may be larger and be held in the palm or by the fingers. The device (190) may include a ring for a single finger and move with that finger. As depicted in FIG. 3, the device (190) body may be wider and narrower near the support (130) or applicator wheel to facilitate application.

The device (190) may include identifying information on the outside to describe the product or provide instructions. The device (190) may include areas that include texturing, over molded rubber, or similar elements to aid in gripping and control of the device (190).

In some examples, the device (190) may include a guide or similar skin contacting element that precedes the support (130) over the skin (100). In one example, the guide includes a cleaning element.

In some examples, the device (190) includes multiple supports (130) to accommodate a number of different products (120). For instance, one portion of the device (190) may dispense a cleaner or pretreatment and another portion may dispense a treatment to be applied in conjunction with the pretreatment. The tapes (110) used for the two applications may be different, for instance the pretreatment may be loaded onto a felt tape (110) loaded with a cleansing agent and the treatment may be loaded onto a nylon tape (110) with a topical therapeutic agent.

The support (130) may be positioned anywhere along the device (190), such as a corner or side of the device (190). In some examples, a portion of the device (190) may be transparent to allow assessment of the amount of unused tape (110) or the amount of used tape (110). Alternately, a window or slit in the device (190) may allow visual assessment of the amount of tape (110). The device (190) may include features to identify the intended direction of motion to dispense the product (120) from the tape (110).

In addition to the previously stated benefits, an additional benefit of the device (190) is that it may be used with a single hand. In some examples the device (190) is pen like. The device (190) may be a smaller size near the support (130) to facilitate visualization of the application site. In other examples, the device (190) is larger to facilitate application over a wider area of the skin. The support (130) may be narrower than the body of the device. The tip of the device (190) with the support (130) may be narrower than the central portion of the device (190) as seen in FIG. 3. Alternately, the device (190) may have a uniform cross-section as seen in FIG. 1. In some examples the device (190) is disposable. In other examples, the device (190) is refillable. The device (190) may include a sterile seal.

In one example, the device (190) is a two-part shell that is loaded with the tape (110) and product (120) and then snap fit or otherwise closed. In some examples the two parts are not of equal thickness. For instance, one part may serves as a mounting platform for the components and the other part may serve as a top piece that locks the components into place. Doing so may avoid a parting line down the middle of the housing and may facilitate molding axes and pins into the housing to reduce the number of parts. In some examples the device (190) is reusable. In such cases, the device (190) may be opened and the used tape (110) replaced with new tape (110). In other examples, the device (190) is disposable and is not designed to open once assembled.

In some examples, the device (190) includes a cap (194). The cap (194) may be a lid or other replaceable sealing element. The cap (194) may be removable or may be hingedly attached to the device. The cap (194) may reduce evaporation of the product (120). For example, the product (120) on the tape (110) may include a volatile component that evaporates under ambient conditions, examples of the volatile component include water and alcohol. Some formulations of the product (120) may include a component that reduces evaporation. Some examples of the device (190) include a temporary or removable seal that reduces evaporation prior to the first use of the product (120). Such a seal may increase shelf life. The seal may cover the exposed tape (110) and the openings the tape (110) passes through from the inside of the device. The device (190) may also reduce communication between the stored unused tape (110) and the ambient environment to reduce evaporation. The cap (194) may include a reflective surface, either flat or curved, to facilitate application of the product (120) to skin (100).

Figure 2:
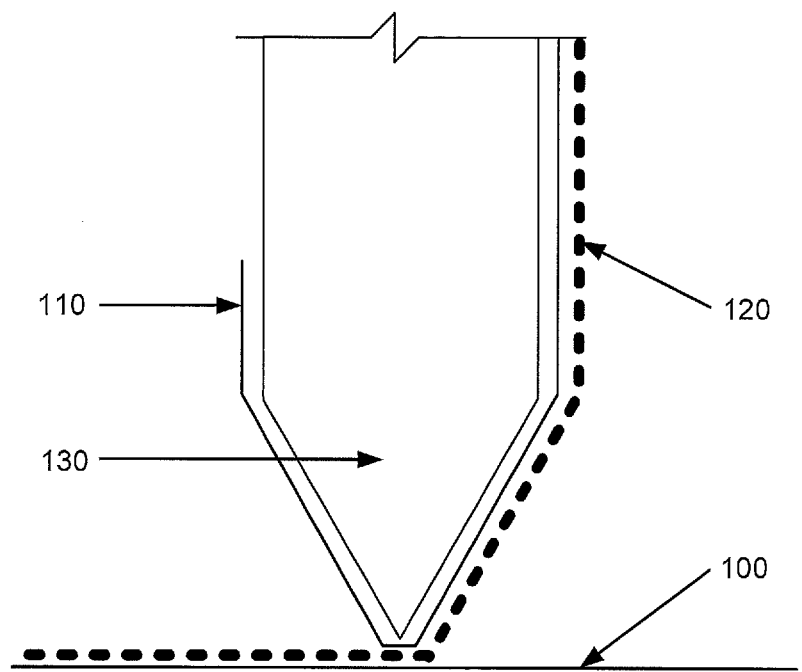
FIG. 2 is a cross-sectional diagram of a device for applying a product to skin according to one example of the principles described herein.

FIG. 2 is a cross-sectional diagram of a device (190) for applying a product (120) to the skin (100) according to one example of the principles described herein. Specifically, FIG. 2 illustrates how the product (120) is transferred from the tape (110) to the skin (100). During use, the tape (110) is passed between the skin (100) and a support (130). As the tape (110) advances, for example via a user moving the device (FIG. 1, 190), the tape (110) comes away from the skin (100) and the product (120) is transferred from the tape (110) to the skin (100). Advancing the device (190) along the skin causes the tape (110) to advance resulting in new tape (110) loaded with product (120) made available for application at the support (130).

In one example, the skin (100) is human skin (100), either living or deceased. The skin (100) may also be is that of a non-human animal.

The tape (110) may be selected from a variety of materials or combinations of materials. In one example, the tape (110) is made using naturally occurring materials such as cotton, linen, wool, silk, hemp, flax, and/or felt. In another example, the tape (110) is made with a polymer material such as polyethylene (PE), high density polyethylene (HDPE), nylon, and/or polytetrafluroethylene (PTFE). In some examples, the tape (110) may be made of both natural and synthetic materials, for instance, a PTFE coating may be applied to one surface of the tape (110) to enhance lubricity or facilitate transfer of the product from the tape to the skin.

The tape (110) has a length, a width, and two surfaces. One surface of the tape (110) has a product (120) disposed on it intended for application to the skin (100). The other surface contacts the support (130) or applicator wheel. The thickness of the tape (110) is small compared with the width and the length of the tape (110).

The tape (110) may include a coating. For instance, the tape (110) may include a coating under the product (120), between the product (120) and the tape (110), to facilitate release of the product (120) from the tape (110). The tape (110) may include a coating on the surface contacting the support (130). For example, the support-contacting surface may include a coating to decrease friction between the support (130) and the tape (110). As will be demonstrated in FIG. 2, the support may be a wheel. The wheel-contacting surface of the tape (110) may include a coating to increase friction between the wheel and the tape (110). Depending upon the particular support (130) selected, the flexibility and strength of the tape (110) may be adjusted to facilitate transfer of the product (120) from the tape (110) to the skin (100). For instance, the path of the tape (110) may include a bend that is easily made by the tape (110) but not by the product (120) which encourages separation of the tape (110) and product (120). If the product (120) is thicker, stiffer, or less flexible than the tape (110), the bend separates the tape (110) and the product (120). Additionally, a bend may concentrate the force on a small area of the tape (110) to product (120) interface while distributing the force over a larger area of the product (120) to skin (100) interface, which may facilitate separation between the tape (110) and product (120). Finally, the bend may induce compression previous to the bend due to the stiffness of the tape, which will increase the contact adhesion between the product (120) and the skin (100). Accordingly, the tape (110) has a minimum strength and flexibility to effectively transfer the product.

The tape (110) may include printed material or coloration to provide information. For instance, the tape (110) may include numbers indicating how much tape (110), and therefore product (120), remains. For example, the tape (110) may include an indicator to indicate that only a small amount of product (120) remains. In some examples, the tape (110) may have a different color for the last portion of the tape. This material may be located on a product-contacting surface of the tape (110) under the product (120) or on the support-contacting surface of the tape (110).

The tape (110) may include multiple products along a length of the tape (110). For instance, a first portion of the tape (110) may include a topical medication and a second portion of the tape (110) may include a protective coating. This allows the topical medication to be applied first and then the protective layer applied over the top of the topical medication. In some applications, the two products are visually distinguishable, for instance by different colors. In another example, the tape (110) may provide information about what product (120) is currently available for dispensing by symbols, colors, text, or other features.

The tape (110) includes a product (120) that is to be applied to the skin (100). The product (120) is disposed on one surface of the tape (110), a surface opposite of a support-contacting surface of the tape (110). In some examples, the product (120) is a layer of relatively uniform thickness that covers the width of the tape (110). One advantage of using a device (190) as disclosed herein is the ability to apply a uniform layer of product (120). For products (120) with a pharmacological effect, this may provide better control of the dosing to the skin (100) with reduced under or over dosing and greater uniformity. For products (120) with an aesthetic effect, this may allow more uniform appearance.

The product (120) disposed on the tape (110) may include a variety of formulations for a variety of applications including medicinal, cosmetic, and recreational. In some examples, multiple layers of product (120) may be disposed on the tape (110). For instance one layer may include a pharmacological agent and another layer may reduce evaporation. Alternately, a layer may provide mechanical protection.

The product (120) may include a wide variety of materials. For example, the product (120) may be a fluid, a liquid, a solution, a solid, a gel, a paste, a cream, a colloid, a slurry, or a mixture of solids and/or liquids that may be stored and applied to the skin (100).

The product (120) may include a topical agent for the treatment of acne. Examples of such materials include salicylic acid, benzoyl peroxide, antibiotics such as tetracycline, etc. The product (120) may include: a topic agent for detection or treatment of a medical condition, a pharmacologically active component, a viscosity modification component, an evaporation modification component, an oil, a color modification component, a dye, a mineral, a metal, an appearance modification component, a compounding agent, a saponification agent, an emulsifier, a solubility modifying agent, a soap, a UV absorbing material, a moisturizer, a cosmetic, an adhesive, and/or a sealant.

In some examples, the product (120) is a non-uniform layer on the tape (110). For example, the product (120) may be shaped. As a specific example, the product (120) may include circular shapes that are sized to cover a skin blemish. As another specific example, the product (120) may be shaped as letters, words, characters, or symbols without significant background material. In another example of a non-uniform layer, the product (120) may be anatomically-shaped, for instance to be placed under the nose or for application to the eyelid. The product (120) may include stripes or patterns applied to the skin (100), where portions of the skin (100) that contact the bare tape (110) receive no product (120). The product (120) may include thinner areas and thicker areas to better accommodate anatomy or provide a desired application profile to the skin (100).

The product (120) may include a layer that includes aesthetic elements that are visible when the product (120) is applied on the skin (100). In another example, a layer may mimic skin (100) appearance to reduce visibility of the applied product (120). A layer of the product (120) may display signs, patterns, symbols, characters, figures, words, numbers, images, glitter, and/or colors. For instance, a layer may include color combinations, logos, sayings, mottos, etc. These may be combined with a medicinal product or may have a purely cosmetic character. For example, the use of symbols may encourage young children to leave the product (120) in place to allow an included topical medication to operate, either because they like the appearance or because it includes a warning symbol.

In one example, the applied product (120) functions as a bandage and includes a clotting agent, antiseptic, antibiotic, and/or similar active ingredients. In one example, the product (120) may include an anti-itch medication such as hydrocortisone, aloe, or similar. In another example, the applied product (120) may include an acne treatment.

The size of the tape (110) and device (FIG. 1, 90) may be selected based on the product (120) being applied, intended user, or other factors. For instance, an emergency bandage may be larger to allow rapid application. In contrast, a bandage for treating children's abrasions may be smaller and include colorful characters. A topical agent for acne treatment may have a small dispensing tip to facilitate placement at the site of a blemish while a sunscreen may be moderately wide to balance precision and speed of application.

The device (190) includes a support (130) for facilitating application of the product (120) to the skin (100). Although shown as a triangle in FIG. 2, the support (130) may be any suitable geometry. The support (130) provides a backing for the tape (110) against the skin (100). This allows the application of pressure to the product (120) to enhance transfer of the product (120) to the skin (100). The pressure also provides tactile feedback to the recipient which facilitates accurate placement. In one example, the support (130) may include a flat surface to press the tape (110) against the skin (100). In another example, the support (130) may include a rounded surface. In one example, the support (130) may include a bend in the path of the tape (110) to facilitate transfer of the product (120) from the tape (110) to the skin (100).

In one example, the support (130) may be rigid or relatively rigid compared to the skin (100). In another example, the support (130) may be flexible. For example, the support (130) may be composed of a flexible material or may include mechanical features to flex the support (130) when pressed. For instance, the support (130) may include a spring that controls the pressure applied to the skin (100). Alternately, the geometry of the support (130) may provide this flexibility.

In some examples, the support (130) is made of a lubricious material that facilitates the sliding of the tape (110) across the support (130). Some examples of such materials include fluropolymers (e.g. PTFE), polyethylene (PE, HDPE, LDPE), polypropylene (PP), polycarbonate (PC), polyurethane, and polyethylene terephthalate (PET). The support (130) may be made of the same material as the body of the device. The support (130) may be a portion of the body of the device. For instance, the support (130) and body of the device (FIG. 1, 190) may be molded as a single piece using injection molding, blow molding, compression molding, thermoforming, or similar techniques. The support (130) may be over molded onto or by the housing material of the device. Alternately, the support (130) may be a separate piece added to the device (FIG. 1, 190) body.

FIG. 3 is a cross-sectional diagram of a system for applying product (120) to skin (100) according to one example of the principles described herein. FIG. 3 depicts the skin (100), tape (110), and product (120) on the tape (110). FIG. 3 also includes an applicator wheel (232) as part of the system. The system includes a tape supplier (240) which stores unused tape (110) and product (120) disposed on the unused tape (110). A tape collector (250) in the housing stores used tape (110) without the product (120), which product (120) has been applied to the skin (100). A belt (260) or other mechanism may connect one or more of the components (232, 240, 250). The system may also include a connection (270) for securing a cap (FIG. 1, 194) to the device. While FIG. 3 depicts an applicator wheel (232), the support (FIG. 2, 130) of FIG. 2 may be used in conjunction with the tape collector (250) and tape supplier (240) as described herein.

The applicator wheel (232) provides support for the tape (110) as well as allowing pressure to be applied to the tape (110) and the skin (100). The applicator wheel (232) may include an axel which allows the applicator wheel (232) to rotate. In some examples, the surface of the applicator wheel (232) is covered or partially covered with a rubber or other high friction material to reduce slipping between the applicator wheel (232) and the tape (110). The applicator wheel (232) surface may be flat or may include texturing, ridges, cross-hatching, or other mechanical features to keep the tape (110) positioned properly. In one example, the applicator wheel (232) includes flanges on the edges of the tape-contacting surface to center the tape (110). In another example, centering the tape (110) on the applicator wheel (232) is facilitated by a guide at the exit from the device (FIG. 1, 190) to the applicator wheel (232). The applicator wheel (232) may transfer force to other elements of the system using the tape (110) and/or by other connections such as gears, belts (260), or similar mechanical devices. For example, the force transferred to the tape (110) as the applicator wheel (232) is pressed against the skin (110) and moved may cause the tape (110) to advance off the tape supplier (240). This may help control the rate of release of the tape (110) from the tape supplier (240) or may help maintain tension on the used tape (110). The applicator wheel (232) may include a lock or brake that prevents the applicator wheel (232) from rotating unless unlocked. In one example, the lock may be activated by placing a cap (FIG. 1, 194) onto the applicator. The lock may be released by removing the cap (FIG. 1, 194) or by pressing a button, slide, or similar element. The applicator wheel (232) may be larger or smaller than the tape supplier (240) or tape collector (250). The applicator wheel (232) or support (130) may be located on a surface of the applicator, on a shoulder, or on a corner of the device (FIG. 1, 190).

In some examples, unused tape (110) and product (120) disposed on the unused tape (110) may be stored in a tape supplier (240) before being advanced to the support (FIG. 1, 130) or applicator wheel (232) for application. In some examples, the tape supplier (240) is a wheel with tape (110) around the wheel. The tape supplier (240) may include an axel and a ring around the axel on which the tape (110) is rolled up. The tape supplier (240) may include a pair of circumferential flanges such that the tape supplier (240) has the form of spool or bobbin. Alternately, the inside surfaces of the device (190) may act as one or both of the flanges that keep the tape (110) positioned properly on the tape supplier (240). In one example, the axel of for the tape supplier (240) is molded into the surface of the device (FIG. 1, 190) such that the tape supplier (240) includes a hub and is loaded over the axel and the tape (110) is threaded over the applicator wheel (232) or support (130). In another example, the tape supplier (240) does not contain a hub but instead contains an opening in the center of a roll of tape to accommodate an axel on the device, a portion of the tape serving as the hub of the wheel. In another example, there is no axel in the center of the tape supplier and the portion of the tape rests against a surface. In such an example, the tape (110) unrolls from the tape supplier (240) as pressure is exerted on a portion of the tape (110) pressed against the skin (100). The surface may be continuous and/or may have one or more pins that prevent travel of the roll of tape and causes it to unroll under tension is applied to the tape (110). The tape supplier (240) and tape collector (250) may be supplied as a cassette, to facilitate replacement of the tape (110) without the user having to thread a replacement tape into a tape collector (250). While FIG. 3 depicts a round tape supplier (240), the tape supplier (240) may be any suitable geometry. Moreover, while FIG. 3 depicts a tape supplier (240) as round, the tape supplier (240) may include two or more axes connected with a belt or tape (110) forming a loop for storing the tape (110) and corresponding product (120). This approach may allow a device (FIG. 1, 190) to store more tape (110) while maintaining a relatively thin profile. In other examples, the tape supplier (240) is a wheel.

The tape supplier (240) may move due to force from the tape (110) and/or the applicator wheel (232). For example, as the applicator wheel (232) is pressed against the skin (100) and moved, the tape (110) may advance. The force causes the tape supplier (240) to move, dispensing tape (110) that is advanced to the support (130). For instance, a belt (260), gears, or similar mechanical component may connect the applicator wheel (232) and tape supplier (240) to regulate speed of rotation or tension on the tape (110). The axes of the various components (tape supplier (240), applicator wheel (232), and tape collector (250)) may be of the same size or may be of varying sizes to better support appropriate force transfer. The tape supplier (240) may include a brake or similar element that helps prevent motion of the tape supplier (240) when the device (FIG. 1, 190) is not applying product (120). The brake may be carried out via a friction contact between a flange and a pin, the applicator shell, or specially designed element. The applicator wheel (232), tape supplier (240), and/or tape collector (250) may include a one-way ratchet to control or regulate rotation.

The tape collector (250) stores the used tape (110) to reduce contact of the used tape (110) with the skin (100). This reduces the chance for contamination of the skin (100) from microbes or material that may have transferred to the tape (110) during an earlier application.

In one example, the used tape (110) is fed outside the device (FIG. 1, 190) to be trimmed, ripped off, or otherwise removed. In another example, the used tape (110) is fed into a tape collector (250) that retains the used tape (110). The tape collector (250) may include a space that accommodates the used tape. The space may be circular, oval, or otherwise shaped to allow collection of the used tape (110). The space may on an interior portion of the device (FIG. 1, 190) housing. In one example, the tape collector (250) maintains tension on the tape (110) and does not store the used tape (110).

As described above, any number of the components (250, 240, 232) may rotate freely or may be joined to operate together. While FIG. 3 depicts one exemplary orientation of the components (250, 240, 232) the components may be oriented in any number of forms. For example, the components may be coplanar. Alternately, the components may be offset from each other. For example, the tape collector (250) may be located further from the support (130) or applicator wheel (232) than the tape supplier (240). In another example, the tape collector (250) may be located closer to the applicator wheel (232) or support (130) than to the tape supplier (240). Similarly, while FIG. 3 depicts particular sizes of wheels for these components (250, 240, 232) the components may be of any size relative to another. For example, the tape collector (250) may be smaller than the tape supplier (240) or the applicator wheel (232). As described above, the components (250, 240, 232) may be linked together or otherwise mechanically coupled to transfer force or control or coordinate rotation. In one example, this is accomplished with a belt (260). In another example this may be accomplished using a number of gears or a shared axis. Mechanical elements may be used to create or regulate friction on the various components. Finally it may make sense for the tape collector (250) to have a larger axis than the tape supplier (240) to facilitate maintaining tension on the used tape (110).

Figure 4:
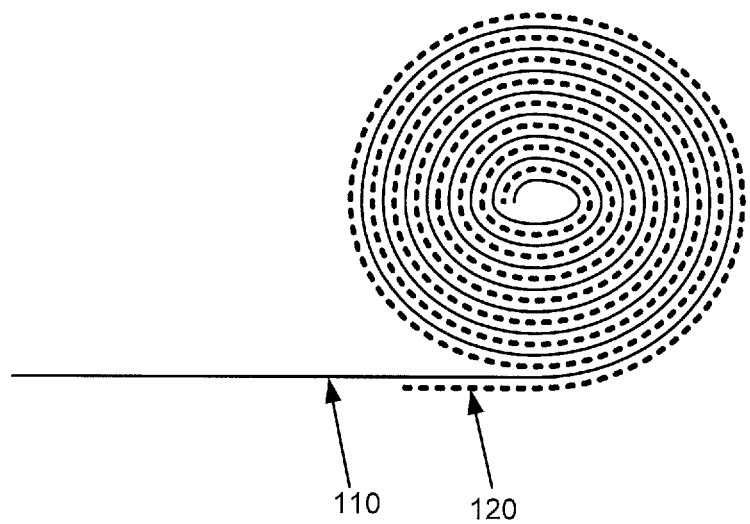
FIG. 4 is a diagram of the tape and product during application according to one example of the principles described herein.

FIG. 4 is a diagram of the tape (110) and product (120) during application according to one example of the principles described herein. In some examples, the tape (110) is in a roll and is stored in the device (FIG. 1, 190), for example, on the tape supplier (FIG. 2, 240). In some examples, the tape (110) may be a part of an assembled device (FIG. 1, 190). In this example, the device (FIG. 1, 190) may be disposable. In other examples, the roll of tape (110) is a replacement component for the assembled device (FIG. 1, 190). In this example, the device (FIG. 1, 190) may be designed to be opened and replace the used tape (110).

The tape (110) includes a product (120) applied to one surface. The tape (110) is then rolled to allow for compact storage of the tape (110). The rolled tape (110) may include an opening in the middle of the roll that is placed over an axel in the applicator shell. In another example, the rolled tape (110) may not have an opening and may instead unroll under contact with walls, pins, restraints, or similar mechanical features of the device.

In some examples, the roll of tape (110) may include a release agent on a non-product surface of the tape (110). The release agent helps to reduce sticking between the product (120) and the tape (110) when the tape is rolled and a support contacting surface of the tape (110) contacts the product (120). The release agent may also be disposed on both sides of the tape (110). In one example, the release agent is a layer of a material, such as PTFE or PE. In another example, the release agent is a fluid, such as polyethylene glycol (PEG), polydimethylsiloxane (PDMS), oils, or greases. In yet another example, the release agent is a powder, such as talc or cornstarch. Selection of a release agent may depend upon the tape (110) material and product (120) to be applied to the skin (100).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A system for applying a product to skin, the system comprising:
   a housing;
   a product to be applied to a skin surface, the product comprising an acne medication;
   a tape disposed in the housing, the tape having the product disposed on one surface, in which:
     the tape moves relative to the housing; and
     the product is removably coupled to the tape such that when the tape moves across the skin the product transfers from the tape to the skin; and
     the tape is made of felt and is in a roll;
   a delivery system to allow application of the product to the skin, in which the delivery system includes:
     a tape supplier to initially store the tape and an unused portion of the product;
     a tape collector to receive a used portion of the tape after the product has been transferred to the skin; and
     a support disposed between the tape supplier and the tape collector to exert force against the skin to facilitate transfer of the product from the tape to the skin.

2. The system of claim 1, in which the support is an applicator wheel.

3. The system of claim 1, in which the product further comprises one of a viscosity agent and an evaporation control agent.

4. The system of claim 2, in which rotation of the at least one of the tape supplier, tape collector, and applicator wheel advances one of the other components.

* * * * *